US007642329B2

(12) United States Patent
Kedar et al.

(10) Patent No.: US 7,642,329 B2
(45) Date of Patent: *Jan. 5, 2010

(54) OLIGOMERIC LACTIDE MACROMER BASED COPOLYMER AND A PROCESS FOR THE PREPARATION THEREOF

(75) Inventors: Suvarnapathaki Rupali Kedar, Pune (IN); Kulkarni Mohan Gopalkrishna, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 343 days.

This patent is subject to a terminal disclaimer.

(21) Appl. No.: 11/518,359

(22) Filed: Sep. 7, 2006

(65) Prior Publication Data

US 2007/0072996 A1 Mar. 29, 2007

(30) Foreign Application Priority Data

Sep. 27, 2005 (IN) .................... 2598/DEL/2005

(51) Int. Cl.
*C08F 218/02* (2006.01)
*C08F 26/00* (2006.01)
(52) U.S. Cl. .................. 526/319; 526/310; 526/258; 526/307.2; 526/307.7; 526/219.6
(58) Field of Classification Search ................ 526/319, 526/310, 258, 307.2, 307.7, 219.5
See application file for complete search history.

(56) References Cited

U.S. PATENT DOCUMENTS

| 6,225,429 B1 * | 5/2001 | Chuang et al. .............. 526/264 |
| 6,998,456 B1 * | 2/2006 | Mallapragada et al. ... 526/328.5 |
| 2007/0073014 A1 * | 3/2007 | Kedar et al. .............. 526/219.6 |

OTHER PUBLICATIONS

Eguiburu et al., Polymer, vol. 37, No. 16, 1996, pp. 3615-3622.*
Park et al., Jan. 3, 2000, Macrmol. Rapid Commun., 21, No. 8, pp. 464-471.*
S.W. Shalaby and R.A. Johnson In: S.W. Shalaby, Editor; Biomedical polymers: Designed to degrade systems, Chapter 1, Carl Hanser Verlag, Munich (1994), pp. 1-34.
R.L. Dunn, Ph.D.: J.O. Hollinger, Editor; Biomedical applications of synthetic biodegradable polymers, Chapter 2, CRC Press, Boca Raton (1995), pp. 17-31.
V. Maquet and R. Jerome; Design of Macroporous Biodegradable Polymer Scaffolds for Cell Transplantation; Materials Science Forum vol. 250 (1997), pp. 15-42.
D.E. Perrin and J.P. English In: A.J. Domb, J. Kost and D.M. Wiseman, Editors, Polyglycolide and Polylactide; Handbook of Biodegradable Polymers, Harwood Academic Publishers, Amsterdam (1997), pp. 3-27.
D.K. Han and J.A. Hubbell; Synthesis of Polymer Network Scaffolds from L-Lactide and Poly(ethylene glycol) and Their Interaction with Cells; Macromolecules (1997), pp. 6077-6083.

G. Coullerez, C. Lowe, P. Pechy, H.H. Kausch and J. Hilborn; Synthesis of Acrylate Functional Telephelic Poly (lactic acid) Oligomer by Transesterification; Journal of Materials Science: Mater. Med. 11 (2000), pp. 505-510.
Matthias Schnabelrauch, Sebastian Vogt, Yves Larcherb and Ingo Wilke; Biodegradable Polymer Networks based on Oligolactide Macromers: Synthesis, Properties and Biomedical Applications; Biomolecular Engineering, 19 (2002), pp. 295-298.
Ryner, M.; Finne, A.; Albertsson, A. C.; and Kricheldorf, H. R.; L-Lactide Macromonomer Synthesis Initiated by New Cyclic Tin Alkoxides Functionalized by Brushlike Structures; Macromolecules 34, (2001) pp. 7281-7287.
Finne, Anna and Albertsson, Ann-Christine; New Functionalized Polyesters to Achieve Controlled Architectures; Journal of Polymer Science, Part A: Polymer Chemistry 42(3), (2004), pp. 444-452.
Zhang, Yeli and Chu, Chih-Chang; Thermal and Mechanical Properties of Biodegradable Hydrophilic-Hydrophobic Hydrogels based on Dextran and Poly (lactic acid); Journal of Materials Science: Materials in Medicine 13 (2002), pp. 773-781.
Wang, Chau-Hui and Hsiue, Ging-Ho; Synthesis and Characterization of Temperature- and pH- Sensitive Hydrogels Based on Poly (2-ethyl-2-oxazoline) and Poly (D,L-Lactide); Journal of Polymer Science, Part A: Polymer Chemistry 40 (8), (2002), pp. 1112-1121.
Hans, Parvez I.; Vogt, S.; Berger, S.; Wilke, I.; Larcher, Y.; Weisser, J.; Schnabelrauch, M.; Design of Oligolactone-Based Scaffolds for Bone Tissue Engineering; Bio-Medical Materials and Engineering 15 (2005), pp. 73-85.
Eun Seok Gil and Samuel M. Hudson;Stimuli-Responseive Polymers and their Bioconjugates and Prog. Polym. Sci. 29 (2004) pp. 1173-1222.
M. Okubo, H. Ahmad and T. Suzuki; Synthesis of Temperature-Sensitive Micron-Sized Monodispersed Composite Polymer Particles and its Application as a Carrier for Biomolecules; Colloid Polym Sci 276 (1998), pp. 470-475.
Li Fu-Mian; Chen, Shuang-Ji; Du, Fu-Sheng; Wu, Zhi-Qiang; Li, Zi-Chen; Stimuli-Responsive Behavior of N,N-Dimethylaminoathyl Methacrylate Polymers and Their Hydrogels; ACS Symposium Series 726 (1999), pp. 266-276.
El-Hag Ali Said, Amr.; Radiation Synthesis of Interpolymer Polyelectrolyte Complex and its Application as a Carrier for Colon-Specific Drug Delivery Systems; Biomaterials 26(15), (2005), pp. 2733-2739.
Yuk, Soon Hong; Seo, Jung Ki; Lee, Jin Ho; Cho, Sun Hang; Application of pH- and Temperature-Sensitive Polymers for Controlled Drug Release Device; ACS Symposium Series 752 (2000), pp. 232-242.
Yuk, Soon Hong; Cho, Sun Hang; Lee, Sang Hoon. pH/Temperature-Sensitive Polymers for Glucose-Sensitive Insulin Delivery; American Chemical Society; Polymer Preprints 39(2), (1998), pp. 204-205.
Kim, E. J.; Cho, S. H.; Yuk, S. H.; Polymeric Microspheres Composed of pH/Temperature-Sensitive Polymer Complex; Biomaterials 22 (2001), pp. 2495-2499.

(Continued)

*Primary Examiner*—Satya B Sastri
(74) *Attorney, Agent, or Firm*—Knobbe Martens Olson & Bear LLP

(57) ABSTRACT

A macromer based novel copolymer comprising an acrylate or methacrylate ester of low molecular weight oligomeric lactide copolymerized with basic monomer is provided. These copolymers show unusual dissolution behavior in that they are soluble over a wide range of pH from 1.8 to 7.4. This unexpected solubility behavior can be exploited to develop pharmaceutical dosage forms.

9 Claims, No Drawings

OTHER PUBLICATIONS

Yuk, Soon Hong; Cho, Sun Hang; Lee, Sang Hoon; Seo, Jung Ki; Lee, Jin Ho. Editor(s): Ottenbrite, Raphael M.; Kim, Sung Wan. Polymeric Drugs & Drug Delivery Systems (2001), pp. 39-55.

Falamarzian, M. and Varshosaz; The Effect of Structural Changes on Swelling Kinetics of Polybasic/Hydrophobic pH-Sensitive Hydrogels; J. Drug Development and Industrial Pharmacy 24(7), (1998), pp. 667-669.

Muehlebach, Andreaas; Synthesis of Well Defined Macromonomers from Polymers made by Atom Transfer Radical Polymerization (ATRP): Amphiphilic Comb-Copolymers and their Applications; Polymeric Materials Science and Engineering 90, (2004), pp. 180.

Traitel, Tamar; Cohen, Yachin; Kost, Joseph; Characterization of Glucose-Sensitive Insulin Release Systems in Simulated In vivo Conditions; Biomaterials 21 (2000), pp. 1679-1687.

M.J. Alonso, M.L. Lorenzo-Lamosa, M. Cuna, J.L. Vila-Jato and D. Torres; Development of a Microencapsulated Form of Cefuroxime Axetil Using pH-Sensitive Acrylic Polymers; Journal of Microencapsulation, 1997, vol. 14, No. 5, 607-616.

Kari Hiltunen, Mika Harkonen, Jukka Seppala, and Taito Vaananen; Synthesis and Characterization of Lactic Acid Based Telechelic Prepolymers; Macromolecules 29, 1996, pp. 8677-8682.

\* cited by examiner

OLIGOMERIC LACTIDE MACROMER BASED COPOLYMER AND A PROCESS FOR THE PREPARATION THEREOF

FIELD OF THE INVENTION

A macromer based copolymer composition comprising a lactide macromer and a basic monomer and method for the preparation of these copolymers are provided. In particular a composition comprising an acrylate or methacrylate ester of oligomeric lactide is provided. These copolymers exhibit unusual dissolution behavior. They are soluble over wide range of pH from 1.8 to 7.4. This dissolution property can be exploited in designing pharmaceutical dosage forms.

BACKGROUND OF THE INVENTION

Biodegradable polyesters derived from aliphatic hydroxy carboxylic acids have been developed for medical applications such as surgical sutures, drug delivery devices, tissue supports, and implants for internal bone fixation (S. W. Shalaby and A. Johnson In: S. W. Shalaby, Editor, Biomedical polymers: Designed to degrade systems, Carl Hanser Verlag, Munich (1994), pp. 1-34. R. L. Dunn In: J. O. Hollinger, Editor, Biomedical applications of synthetic biodegradable polymers, CRC Press, Boca Raton (1995), pp. 17-31. V. Maquet and R. Jerome Mater. Sci. Forum 250 (1997), pp. 15-42).

Most of these materials are made from high-molecular-weight linear polyesters like polylactides, polyglycolides and their copolymers (D. E. Perrin and J. P. English In: A. J. Domb, J. Kost and D. M. Wiseman, Editors, Handbook of biodegradable polymers, Harwood Academic Publishers, Amsterdam (1997), pp. 3-27). Less attention has been paid to oligomeric esters, because these oligomers normally do not have the mechanical and thermal properties required for sutures or implants. Recent work on synthesis of liquid or low melt oligolactides offers interesting approach to a new class of biodegradable materials useful for injectable drug delivery systems, implant coatings or soft tissue augmentations. In addition, biodegradable polymer networks and composites can be prepared from these oligoesters terminated with unsaturated functional groups (D. K. Han and J. A. Hubbell Macromolecules 30 (1997), pp. 6077-6083, G. Coullerez, C. Lowe, P. Pechy, H. H. Kausch and J. Hilborn J. Mater. Sci: Mater. Med. 11 (2000), pp. 505-510).

Novel linear and star-shaped oligolactide macromers were prepared and used for the fabrication of highly porous polymer network scaffolds of controlled shape. In vitro studies on the cultivation of osteoblasts on these materials demonstrated that the polymer networks possess excellent biocompatibility and they are well suited as scaffolds for bone tissue engineering. (Matthias Schnabelrauch, Sebastian Vogta, Yves Larcherb and Ingo Wilkeb, Biomolecular Engineering, 19 (2-6), (2002), pp. 295-298).

Controlled ring-opening polymerization of L-Lactide was initiated using cyclic tin alkoxides which resulted in series of lactide macromonomers. Double bond of the initiator was successfully incorporated into the synthesized macromonomers which is well-suited for postpolymerization into a brushlike polymer. (Ryner, M.; Finne, A.; Albertsson, A. C.; Kricheldorf, H. R. Macromolecules 34, (2001) pp. 7281-7287). This unsaturated macromonomer provided a variety of opportunities for further modifications. The incorporated C=C double bond was oxidized into epoxides. (Finne, Anna; Albertsson, Ann-Christine. Journal of Polymer Science, Part A: Polymer Chemistry 42(3), (2004), pp. 444-452).

Poly (D, L) lactide diacrylate macromer was used to develop a new family of biodegradable hydrogels with photo-crosslinked dextran derivative of allyl isocyanate. The changes in thermal and mechanical properties of these hydrogels as function of dextran and lactide macromer composition were investigated. (Zhang, Yeli; Chu, Chih-Chang. Journal of Materials Science: Materials in Medicine 13(8), (2002), pp. 773-781).

A series of temperature and pH-sensitive hydrogels based on poly (2-ethyl-2-oxazoline) and three-arm poly (D, L-lactide) macromer were synthesized via photo-copolymerization. Lactide macromer was synthesized by first reacting lactide with Glycerol and then reacting 3 arm poly-lactide with methacryloyl chloride and triethylamine. This study effectively proved that unique combination of water swellability and biodegradability properties provides hydrogels for a much wider range of applications in biomedical fields. (Wang, Chau-Hui; Hsiue, Ging-Ho. Journal of Polymer Science, Part A: Polymer Chemistry 40(8), (2002), pp. 1112-1121).

Difunctional oligolactone macromers were synthesized by ring-opening oligomerization of various lactones (L-lactide, glycolide, p-dioxanone) in the presence of suitable diols (propane-1,2-diol, dianhydro-D-glucitol) and subsequent end capping of these oligolactones with methacrylate moieties. Highly porous scaffolds were fabricated from these macromers. The oligolactide based polymer networks possess excellent biocompatibility and are promising candidates as scaffolds in bone tissue engineering. (Haris, Parvez I.; Vogt, S.; Berger, S.; Wilke, I.; Larcher, Y.; Weisser, J.; Schnabelrauch, M. Bio-Medical Materials and Engineering 15(1, 2), (2005), pp. 73-85).

Weak polyacids or polybases, which undergo an ionization/deionization transition from pH 4_8, are utilized as pH-responsive polymers. Poly(N,N'-dimethyl amino ethyl methacrylate) (PDMAEMA) and poly(N,N'-diethyl amino ethyl methacrylate) (PDEAEMA) are examples of pH responsive polybases. (Eun Seok Gil, Samuel M. Hudson. Prog. Polym. Sci. 29 (2004) pp. 1173-1222). They have amine groups in their side chains. The amine groups gain protons under acidic condition and release them under basic condition. PDMAEMA was also reported to exhibit temperature sensitivity similar to PNIPAAm (M. Okubo, H. Ahmad and T. Suzuki, Colloid Polym Sci 276 (1998), pp. 470-475). The origin of the thermo-responsive behavior lies in the balance of hydrophobicity and hydrophilicity of poly (DMAEMA), while the pH-sensitive behavior is due to the existence of tertiary amino-group, which gets protonated with decreasing pH of the aqueous medium. These properties of poly (DMAEMA) were used to develop hydrogels having good mechanical properties through copolymerization of DMAEMA with other methacrylate derivatives, among which the copolymers and hydrogels prepared from DMAEMA and Butyl methacrylate (BMA) were studied in detail. By using a unique method and photoredox system to initiate the copolymerization of DMAEMA with BMA, a stable asymmetric bilayer sheet which shows reversible thermal and pH-responsive behavior was developed as intelligent soft material. (Li, Fu-Mian; Chen, Shuang-Ji; Du, Fu-Sheng; Wu, Zhi-Qiang; Li, Zi-Chen. ACS Symposium Series 726 (1999), pp. 266-276).

A pH-sensitive interpolymer polyelectrolyte complex was synthesized by gamma radiation induced copolymerization of acrylic acid and N,N'-Dimethyl amino ethyl methacrylate (DMAEMA). pH dependent swelling showed different phase transitions depending on the copolymer composition and also showed the interpolymer polyelectrolyte complex formation at pH values ranging from pH 3 to pH 4. The ability of the copolymer to be used as drug carrier for colon specific drug delivery system was demonstrated using Ketoprofen as a model drug. (El-Hag Ali Said, Amr. Biomaterials 26(15), (2005), pp. 2733-2739).

A new pH/temperature responsive polymer system with transitions resulting both from polymer-water and polymer-polymer interactions has been demonstrated using the copolymer composed of N,N'-dimethyl amino ethyl methacrylate (DMAEMA) and ethylacrylamide (EAAm) and the mixture of poly DMAEMA and poly EAAm. Based on the pH/temperature responsiveness of the copolymer and polymer mixture, glucose controlled insulin delivery system and microspheres for temperature sensitive solute release were designed and characterized. (Yuk, Soon Hong; Seo, Jung Ki; Lee, Jin Ho; Cho, Sun Hang. ACS Symposium Series 752 (2000), pp. 232-242).

The insulin release from the same copolymer matrix was demonstrated. (Yuk, Soon Hong; Cho, Sun Hang; Lee, Sang Hoon. Polymer Preprints 39(2), (1998), pp. 204-205). Poly (N,N-dimethyl amino ethyl) methacrylate (DMAEMA) and polyethyl acrylamide (EAAm) system was also used to design the microspheres for pH/temperature sensitive drug release. Hydrocortisone was used as a model drug. This gave the control of hydrocortisone release in an on-off manner without considerable lag time (Kim, E. J.; Cho, S. H.; Yuk, S. H. Biomaterials 22(18), (2001), pp. 2495-2499).

In the same way copolymers of DMAEMA and ethylacrylamide (EAAm) [or acrylamide (AAm)] were prepared and characterized as polymeric drug delivery systems modulated for pulsatile and time release. When the temperature of poly DMAEMA aqueous solution was increased above 50° C., the polymer precipitated from the solution. The incorporation of EAAm in the copolymer caused lower critical solution temperature (LCST) to shift to a lower temperature. This was because of the formation of hydrogen bonds, which protect (N,N-dimethyl amino) ethyl groups from exposure to water and led to a hydrophobic contribution to the LCST. Glucose controlled insulin release and thermosensitive permeation of hydrocortisone was accomplished by manipulating pH/temperature responsiveness of polymers. (Yuk, Soon Hong; Cho, Sun Hang; Lee, Sang Hoon; Seo, Jung Ki; Lee, Jin Ho. Editor(s): Ottenbrite, Raphael M.; Kim, Sung Wan. Polymeric Drugs & Drug Delivery Systems (2001), pp. 39-55).

The effect of pendent side-chain length and crosslinking agent concentration in methyl methacrylates/dimethyl amino ethyl methacrylate as polybasic/hydrophobic pH-sensitive hydrogel was studied. Increasing both side-chain length and crosslinking agent concentration decreased the sharpness of response to pH and water-uptake capacity of the polymer. (Falamarzian, M.; Varshosaz, J. Drug Development and Industrial Pharmacy 24(7), (1998), pp. 667-669).

Amphiphilic comb-copolymers made by copolymerization of N, N-dimethyl amino ethyl methacrylate (DMAEMA) and poly (Butyl acrylate) macromonomers are excellent dispersants for many organic pigments in different coating systems. (Muehlebach, Andreas. Polymeric Materials Science and Engineering 90, (2004), pp. 180). The glucose-responsive insulin controlled release system based on the hydrogel poly (2-hydroxyethyl methacrylate-co-N, N-dimethyl amino ethyl methacrylate), with entrapped glucose oxidase, catalase and insulin was studied. When exposed to physiological fluids, glucose diffuses into the hydrogel; glucose oxidase catalyzes the glucose conversion to gluconic acid, causing swelling of the pH-sensitive hydrogel and subsequently increased insulin release. The effects of polymer morphology and oxygen availability on hydrogel swelling and on insulin release kinetics were tested. In vivo experiments on rats demonstrated that at least some of the entrapped insulin retained its active form and was effective in reducing blood glucose levels. Thus the pH-sensitive hydrogel poly (HEMA-co-DMAEMA) could be manipulated to produce glucose-responsive insulin release system that was effective in reducing blood glucose levels. (Traitel, Tamar; Cohen, Yachin; Kost, Joseph. Biomaterials 21(16), (2000), pp. 1679-1687).

Copolymerization of acrylate monomers with basic monomers like Dimethyl amino ethyl methacrylate (DMAEMA) with the aim of designing controlled drug delivery of therapeutic or complex protein molecules like insulin or site specific drug delivery using hydrogels has been reported. Such polymers containing basic functional groups such as amino groups are known to dissolve at pH prevalent in the stomach. Hence these copolymers of acrylates with DMAEMA result in pH sensitive polymers and at times exhibit temperature sensitive behavior. The copolymers have high molecular weights and they are used in variety of applications like drug delivery systems and also as dispersants in pigment industry. DMAEMA along with other neutral methacrylates (Composition of Eudragit E) is also used as reverse enteric coating. This polymer shows swelling at pH 5. Percentage of DMAEMA in Eudragit E is high (35% w/w), which possibly results in negative drug interaction with some of the drugs. (M. J. Alonso, M. L. Lorenzo-Lamosa, M. Cuna, J. L. Vila-Jato and D. Torres, Journal of Microencapsulation, 1997, Volume 14, No. 5, 607-616). Low molecular weight DMAEMA polymers having low basic monomer content and their utility as excipient in pharmaceutical drug delivery has not been investigated in the past.

The preferred embodiments relate to a composition of a low molecular weight macromer based copolymer synthesized using oligomeric lactide macromer and basic monomer. It also demonstrates that at very low concentration of the basic monomer (about 12% w/w) this copolymer exhibits unusual dissolution behavior. Contrary to the solubility behavior of Eudragit E polymers, these polymers are soluble over a wide pH range. These polymers are copolymers of lactide macromer and DMAEMA. Because of their unusual dissolution behavior, they can be used as excipients in pharmaceutical drug delivery systems. The lactide macromer used in the preferred embodiments is a low molecular weight moiety and the copolymer shows unexpected dissolution properties which are very different than copolymers of DMAEMA reported in the literature.

SUMMARY OF THE INVENTION

The preferred embodiments relate to a macromer based novel copolymer comprising low molecular weight lactide macromer and a basic monomer, and a process for the preparation of macromer based novel copolymer by copolymerization of acrylate or methacrylate ester of oligomeric lactide with basic DMAEMA monomer.

Accordingly the preferred embodiments provide a novel oligomeric lactide macromer based copolymer having the general formula

wherein A is an oligomeric lactide macromer having a degree of polymerization in the range of 2 to 10, B is a basic monomer, x varies from 1 to 4, y varies from 3 to 7 and n varies from 1 to 5.

In a preferred embodiment the copolymer prepared is soluble in an aqueous medium over a pH rage of 1.8 to 7.4.

In another preferred embodiment the copolymer prepared has a molecular weight in the range of 1000 to 5000.

In yet another embodiment the content of oligomeric lactide macromer present is in the range of 25 to 90% w/w of the copolymer.

In yet another embodiment the content of basic monomer present is in the range of 10 to 75% w/w of the copolymer.

In yet another embodiment the macromer A used is an acrylic or methacrylic acid ester selected from oligo (lactide) acrylate and oligo (lactide) methacrylate.

In yet another embodiment macromer A used has a molecular weight in the range of 500 to 1000.

In yet another embodiment the basic monomer B used is selected from the group consisting of dimethyl amino ethyl methacrylate, dimethyl amino ethyl acrylate, diethyl amino ethyl methacrylate, diethyl amino ethyl acrylate, piperidine ethyl methacrylate and 2 tert-butyl amino ethyl methacrylate.

The preferred embodiments further provide a process for the preparation of a novel oligomeric lactide macromer based copolymer having the general formula $$[A_{(x)}B_{(y)}]_n$$

wherein A is an oligomeric lactide macromer having a degree of polymerization in the range of 2 to 10, B is a basic monomer, x varies from 1 to 4, y varies from 3 to 7 and n varies from 1 to 5, which comprises preparing a solution of a macromer A and a basic monomer B in an organic solvent, adding a free radical initiator to above said solution mixture and heating it to a temperature ranging between 50 to 75°C., for a period of 16 to 24 hours, concentrating the above said reaction mixture by removing solvent, at a reduced pressure and precipitating the resultant reaction mixture in water to recover the desired copolymer.

In a preferred embodiment the macromer A used is an acrylic or methacrylic acid ester selected from the group consisting of oligo (lactide) acrylate and oligo (lactide) methacrylate In another preferred embodiment the macromer A used has a molecular weight in the range of 500 to 1000.

In a preferred embodiment the basic monomer B used is selected from the group consisting of dimethyl amino ethyl methacrylate, dimethyl amino ethyl acrylate, diethyl amino ethyl methacrylate, diethyl amino ethyl acrylate, piperidine ethyl methacrylate and 2 tert-butyl amino ethyl methacrylate.

In yet another embodiment the organic solvent used is selected from the group consisting of chlorinated hydrocarbon, alcohol, ester, ketone, formamide, tetrahydrofuran, dioxane and dimethyl sulfoxide.

In yet another embodiment the free radical initiator used is an azocompound selected from the group consisting of azo-bis-cyano-valeric acid, azo-bis-biphenyl methane, azo-bis-methyl isobutyrate and azo-bis-isobutyronitrile.

In yet another embodiment the free radical initiator used is selected from the group consisting of peroxide, hydroperoxide, peracid and perester.

In yet another embodiment the copolymer obtained is soluble in an aqueous medium over a pH rage of 1.8 to 7.4.

In yet another embodiment the copolymer obtained has a molecular weight in the range of 1000 to 5000.

In yet another embodiment the copolymer obtained has a content of oligomeric lactide macromer in the range of 25 to 90% w/w of the copolymer.

In still another embodiment the copolymer obtained has a content of basic monomer B in the range of 10 to 75% w/w of the copolymer.

DETAILED DESCRIPTION OF THE PREFERRED EMBODIMENT

High-molecular-weight linear polyesters like polylactides, polyglycolides and their copolymers are widely used for medical applications such as surgical sutures, drug delivery devices, tissue supports, and implants for internal bone fixation. But less attention has been paid to lactide oligomers as they lack mechanical and thermal properties required for above applications. These low melt oligolactides can be looked upon as a new class of biodegradable materials useful in injectable drug delivery systems, implant coatings or soft tissue augmentations.

The preferred embodiments relate to the synthesis of novel lactide copolymers from low molecular weight lactide macromer and basic monomer. Copolymer compositions of the preferred embodiments can be obtained by varying two principal factors in the process.

1. The molecular weight of lactide macromer.
2. Composition of macromer and basic monomer in feed during polymerization In the preferred embodiments the lactide macromer (A) is synthesized from oligo (lactide) diol by condensation reaction with acryloyl chloride or methacryloyl chloride using triethyl amine as base. (Haris, Parvez I.; Vogt, S.; Berger, S.; Wilke, I.; Larcher, Y.; Weisser, J.; Schnabelrauch, M. Bio-Medical Materials and Engineering 15(1, 2), (2005), pp. 73-85)

This macromer can be also synthesized by coupling oligomeric diol with acrylic acid or methacrylic acid using Dicyclohexyl carbodiimide.

Oligomeric lactide diol is an oligomeric lactide having terminal hydroxyl groups which is synthesized from Lactide and 1, 4 Butanediol by ring opening melt polymerization. (Kari Hiltunen, Mika Harkonen, Jukka Seppala, Taito Vaananen Macromolecules 29, 1996, pp. 8677-8682). This oligo (lactide) diol is then dissolved in tetrahydrofuran to which acryloyl chloride is added drop by drop under Nitrogen atmosphere. The product is recovered by removing salt by filtration. Then macromer is precipitated in non-solvent like water and dried at room temperature. This macromer is then used for copolymerization with a basic monomer.

The solution polymerization technique is used for polymerization of oligomeric lactide macromer with basic monomer. In solution polymerization, the macromer and basic monomer are dissolved in the solvent. Azo-bis-isobutyronitrile is used as initiator for polymerization. Reaction mixture is purged with Nitrogen and the polymerization carried out under inert atmosphere. After stipulated reaction time, solvent is evaporated under reduced pressure and the polymer is precipitated from the solution, by precipitating in nonsolvents like water, petroleum ether, or diethyl ether. The polymer is then dried under vacuum.

The dissolution behavior of the polymers synthesized was studied by exposing the polymers to buffer solutions of different range of 1.8, 4.8, 6.8 and 7.4 pH. 50 mg dry polymer of each composition was put in different test tube in 5 ml buffer of different pH.

Dissolution behavior of the polymers is recorded in table 1 and 2.

The preferred embodiments are now illustrated by examples which are representative only and do not in any way limit the scope of the invention.

EXAMPLE 1

This example provides for the preparation of copolymer of poly (Lactide) acrylate with Dimethyl amino ethyl methacrylate in which DMAEMA content is 14% w/w 1.0 g ($1.42 \times 10^{-3}$ moles) poly (Lactide) acrylate was dissolved in 13 ml Dimethyl formamide to which 0.240 ml ($1.42 \times 10^{-3}$ moles) Dimethyl amino ethyl methacrylate was added. The initiator azo bis Isobutyronitrile 9.32 mg ($5.68 \times 10^{-5}$ moles) was added to it. This reaction mixture was stirred well and nitrogen was purged through it for 10 minutes. This was heated for 24 hours at 65° C. in a water bath. After predetermined reaction time, solvent was removed under reduced pressure and the polymer was precipitated in water. Polymer was dried under vacuum and characterized by NMR and VPO.

NMR of the copolymer was recorded in deuterated chloroform. Signals observed in the spectrum which were used for composition analysis were (2 protons of two —CH of lactide at 5.16 with 2 protons of —OCH$_2$ of DMAEMA at 4.2)

EXAMPLE 2

This example provides for the preparation of copolymer of poly (Lactide) methacrylate with Dimethyl amino ethyl methacrylate in which DMAEMA content is 72% w/w 1.0 g ($1.40 \times 10^{-3}$ moles) poly (Lactide) methacrylate was dissolved in 10 ml Dimethyl formamide to which 1.99 g (0.0126 moles) Dimethyl amino ethyl methacrylate was added. The initiator azo bis Isobutyronitrile 45 mg ($2.8 \times 10^{-4}$ moles) was added to it. This reaction mixture was stirred well and nitrogen was purged through it for 10 minutes. This was heated for 18 hours at 60° C. in a water bath. After stipulated reaction time, solvent was removed under reduced pressure and the polymer was precipitated in water. Polymer was dried under vacuum and characterized by NMR and VPO.

EXAMPLE 3

This example provides for the preparation of copolymer of poly (Lactide) acrylate with Dimethyl amino ethyl methacrylate in which poly (lactide) acrylate molecular weight was 700.

1.0 g ($1.42 \times 10^{-3}$ moles) poly (Lactide) acrylate was dissolved in 13 ml Dimethyl formamide to which 0.957 ml ($5.68 \times 10^{-3}$ moles) Dimethyl amino ethyl methacrylate was added. The initiator azo bis Isobutyronitrile 23 mg ($1.42 \times 10^{-4}$ moles) was added to it. This reaction mixture was stirred well and nitrogen was purged through it for 10 minutes. This was heated for 20 hours at 70° C. in a water bath. After predetermined reaction time, solvent was removed under reduced pressure and polymer was precipitated in water. Polymer was dried under vacuum and characterized by NMR and VPO.

EXAMPLE 4

This example provides for the preparation of copolymer of poly (Lactide) methacrylate with Dimethyl amino ethyl methacrylate in which poly (lactide) methacrylate molecular weight was 800.

1.0 g ($1.25 \times 10^{-3}$ moles) poly (Lactide) methacrylate was dissolved in 10 ml Dimethyl formamide to which 0.210 ml ($1.25 \times 10^{-3}$ moles) Dimethyl amino ethyl methacrylate was added. The initiator azo bis Isobutyronitrile 8.21 mg ($5.0 \times 10^{-5}$ moles) was added to it. This reaction mixture was stirred well and nitrogen was purged through it for 10 minutes. This was heated for 22 hours at 55° C. in a water bath. After stipulated reaction time, solvent was removed under reduced pressure and the polymer was precipitated in water. Polymer was dried under vacuum and characterized by NMR and VPO.

Vapour pressure osmometer (VPO) was used for molecular weight measurement of all these DMAEMA copolymers was from KNAUER K 7000 series. Solvent used for measurement was chloroform (HPLC grade).

TABLE 1

Dissolution behavior of polymers in buffers
Composition - oligo (Lactide) acrylate:DMAEMA

| Molecular weight of oligo (lactide) acrylate | Composition of the copolymers (moles) In feed | Composition of the copolymers (moles) By NMR | DMAEMA content % w/w of the copolymer | Molecular weight of copolymer | Dissolution in buffers of pH 1.8, 4.8, 6.8 and 7.4 |
|---|---|---|---|---|---|
| 750 | 10:90 | 26:74 | 39 | 4699 | Polymer dissolved in all buffers within 30 minutes |
| 700 | 20:80 | 27:73 | 38 | 4598 | Polymer dissolved in all buffers within 30 minutes |
| 700 | 30:70 | 43:57 | 23 | 1135 | Polymer dissolved in all buffers within 45 minutes |
| 700 | 40:60 | 52:48 | 17 | 1055 | Polymer dissolved in all buffers within 1 hour |
| 700 | 50:50 | 59:41 | 14 | 1372 | Polymer dissolved in all buffers within 1 hour |

TABLE 2

Dissolution behavior of polymers in buffers
Composition: oligo (lactide) methacrylate:DMAEMA

| Molecular weight of oligo (lactide) methacrylate | Composition of the copolymers (moles) In feed | Composition of the copolymers (moles) By NMR | DMAEMA content % w/w of the copolymer | Molecular weight of copolymer | Dissolution in buffers of pH 1.8, 4.8, 6.8 and 7.4 |
|---|---|---|---|---|---|
| 710 | 10:90 | 8:92 | 72 | 4865 | Polymer dissolved in 10 minutes in all buffers |
| 710 | 20:80 | 28:72 | 36 | 2810 | Polymer dissolved in 20 minutes in all buffers |
| 710 | 30:70 | 31:69 | 33 | 2746 | Polymer dissolved in 20 minutes in all buffers |
| 710 | 40:60 | 36:64 | 28 | 2680 | Polymer dissolved in 30 minutes in all buffers |

TABLE 2-continued

Dissolution behavior of polymers in buffers
Composition: oligo (lactide) methacrylate:DMAEMA

| Molecular weight of oligo (lactide) methacrylate | Composition of the copolymers (moles) In feed | By NMR | DMAEMA content % w/w of the copolymer | Molecular weight of copolymer | Dissolution in buffers of pH 1.8, 4.8, 6.8 and 7.4 |
|---|---|---|---|---|---|
| 710 | 50:50 | 41:59 | 24 | 2435 | Polymer dissolved in 30 minutes in all buffers |
| 800 | 50:50 | 58:42 | 12 | 1170 | Polymer dissolved in 45 minutes in all buffers. |

Advantages of the copolymer of the preferred embodiments are: 1) it exhibits unusual dissolution behavior and are soluble in aqueous medium over a wide pH range of 1.8 to 7.4; 2) because of their unusual dissolution behavior, they can be used as excipients in pharmaceutical drug delivery systems; and 3) the lactide macromer used in the present invention is a low molecular weight moiety.

All references cited herein, including but not limited to published and unpublished applications, patents, and literature reference, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An oligomeric lactide macromer based copolymer having a general formula $[A_{(x)}B_{(y)}]_n$ wherein A is an oligomeric lactide macromer selected from the group consisting of oligo (lactide) acrylate and oligo (lactide) methacrylate and having a degree of polymerization of from 2 to 10; B is a basic monomer; selected from the group consisting of dimethyl amino ethyl methacrylate, dimethyl amino ethyl acrylate, diethyl amino ethyl methacrylate, diethyl amino ethyl acrylate, piperidine ethyl methacrylate and 2-tert-butyl amino ethyl methacrylate; x is from 1 to 4; y is from 3 to 7; and n is from 1 to 5, wherein a molecular weight of the oligomeric lactide macromer is from 500 to 1000, wherein the copolymer has a molecular weight of from 1000 to 5000, and wherein the copolymer is soluble in an aqueous medium at a pH of from 1.8 to 7.4.

2. The copolymer of claim 1, wherein a content of oligomeric lactide macromer is from 25% w/w to 90% w/w of the copolymer.

3. The copolymer of claim 1, wherein a content of basic monomer is from 10% w/w to 75% w/w of the copolymer.

4. A process for the preparation of an oligomeric lactide macromer based copolymer,
   which comprises:
   preparing a solution of an oligomeric lactide macromer selected from the group consisting of oligo (lactide) acrylate and oligo (lactide) methacrylate and having a degree of polymerization of from 2 to 10 and basic monomer selected from the group consisting of dimethyl amino ethyl methacrylate, dimethyl amino ethyl acrylate, diethyl amino ethyl methacrylate, diethyl amino ethyl acrylate, piperidine ethyl methacrylate and 2-tert-butyl amino ethyl methacrylate; in an organic solvent;
   adding a free radical initiator to the solution and heating it to a temperature of from 50 to 75° C., for a period of from 16 to 24 hours, whereby a reaction mixture is obtained;
   concentrating the reaction mixture by removing organic solvent, at a reduced pressure; and
   precipitating the concentrated reaction mixture in water to recover the oligomeric lactide macromer based copolymer having a general formula:

$[A_{(x)}B_{(y)}]_n$ wherein A is the oligomeric lactide macromer; B is the basic monomer; x is from 1 to 4; y is from 3 to 7; and n is from 1 to 5, wherein the oligomeric lactide macromer has a molecular weight of from 500 to 1000, wherein the copolymer has a molecular weight of from 1000 to 5000, and wherein the copolymer is soluble in an aqueous medium at a pH of from 1.8 to 7.4.

5. The process of claim 4, wherein the organic solvent is selected from the group consisting of chlorinated hydrocarbon, alcohol, ester, ketone, formamide, tetrahydrofuran, dioxane, and dimethyl sulfoxide.

6. The process of claim 4, wherein the free radical initiator is selected from the group consisting of azo compound, peroxide, hydroperoxide, peracid, and perester.

7. The process of claim 6, wherein the azo compound is selected from the group consisting of azo-bis-cyano-valeric acid, azo-bis-biphenyl methane, azo-bis-methyl isobutyrate, and azo-bis-isobutyronitrile.

8. The process of claim 4, wherein the copolymer has a content of oligomeric lactide macromer of from 25% w/w to 90% w/w of the copolymer.

9. The process of claim 4, wherein the copolymer has a content of basic monomer of from 10% w/w to 75% w/w of the copolymer.

* * * * *

UNITED STATES PATENT AND TRADEMARK OFFICE
CERTIFICATE OF CORRECTION

| | | |
|---|---|---|
| PATENT NO. | : 7,642,329 B2 | Page 1 of 2 |
| APPLICATION NO. | : 11/518359 | |
| DATED | : January 5, 2010 | |
| INVENTOR(S) | : Suvarnapathaki Rupali Kedar et al. | |

It is certified that error appears in the above-identified patent and that said Letters Patent is hereby corrected as shown below:

On page 1, at column 1, item 56, line 8, under Other Publications, please change "Macrmol." to --Macromol.--.

On page 1, at column 2, item 56, line 24, under Other Publications, please change "Hans," to --Haris,--.

On page 1, at column 2, item 56, line 28, under Other Publications, please change "Responseive" to --Responsive--.

On page 1, at column 2, item 56, line 36, under Other Publications, please change "Dimethylaminoathyl" to --Dimethylaminoethyl--.

On page 2, at column 1, item 56, line 9, under Other Publications, please change "Andreaas" to --Andreas--.

On page 2, at column 2, item 56, line 2, under Other Publications, please change "vivo" to --Vivo--.

Col. 5, line 38, after "acrylate" please insert --.--.

Col. 6, line 24, after "polymerization" insert --.--.

Col. 6, line 32, after "73-85)" please insert --.--.

Col. 7, line 9, after "w/w" please insert --.--.

Signed and Sealed this

Fourteenth Day of September, 2010

David J. Kappos
*Director of the United States Patent and Trademark Office*

CERTIFICATE OF CORRECTION (continued)
U.S. Pat. No. 7,642,329 B2

Col. 7, lines 9-19, please delete "1.0 g (1.42x................NMR and VPO." and insert the same on Col. 7, Line 10, as a new paragraph.

Col. 7, line 23, after "4.2)" please insert --.--.

Col. 7, line 29, after "w/w" insert --.--.

Col. 10, line 1, in Claim 1, change "monomer;" to --monomer--.

UNITED STATES PATENT AND TRADEMARK OFFICE
CERTIFICATE OF CORRECTION

PATENT NO. : 7,642,329 B2  Page 1 of 1
APPLICATION NO. : 11/518359
DATED : January 5, 2010
INVENTOR(S) : Kedar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this

Twenty-first Day of December, 2010

David J. Kappos
*Director of the United States Patent and Trademark Office*